United States Patent [19]
Andersson et al.

[11] 4,144,768
[45] Mar. 20, 1979

[54] APPARATUS FOR ANALYZING COMPLEX ACOUSTIC FIELDS WITHIN A DUCT

[75] Inventors: Anders O. Andersson, Seattle; Robert B. Purves, Kent, both of Wash.

[73] Assignee: The Boeing Company, Seattle, Wash.

[21] Appl. No.: 866,390

[22] Filed: Jan. 3, 1978

[51] Int. Cl.² .................................... G01N 29/02
[52] U.S. Cl. ................................ 73/646; 73/649
[58] Field of Search ............ 73/646, 645, 647, 648, 73/649, 658, 659, 661, 24, 579

[56] References Cited
U.S. PATENT DOCUMENTS

| | | | |
|---|---|---|---|
| 1,528,586 | 3/1925 | Tate | 73/24 |
| 3,009,104 | 11/1961 | Brown | 73/597 |
| 3,434,334 | 3/1969 | Vandenbussche | 73/24 |
| 3,533,485 | 10/1970 | Buffum et al. | 73/599 |
| 3,781,782 | 12/1973 | Scott et al. | 73/649 |
| 3,824,842 | 7/1974 | Wiat et al. | 73/589 |

*Primary Examiner*—Stephen A. Kreitman
*Attorney, Agent, or Firm*—Christensen, O'Connor, Johnson & Kindness

[57] ABSTRACT

A system for resolving a complex acoustic field, resulting when acoustic energy propagates through a duct, into component unit spatial pressure patterns or modes is disclosed. In each disclosed system arrangement, an acoustic filter, which includes one or more annular cavities, circumferentially surrounds the duct through which the acoustic energy propagates and sound is coupled from the duct into one end of each annular filter cavity via a series of openings which exhibit a relatively high acoustic impedance and a relatively high resistance to fluid flow. Each filter cavity is dimensioned such that it is excited into resonance when the circumferential distance between adjacent nodes of a modal component of the pressure pattern within the duct is mathematically related to the velocity of sound within a filter cavity by a predetermined factor. When a cavity resonates, maximum acoustic pressure transfer occurs between the duct and two or more microphones that are circumferentially spaced apart from one another along the second end of each annular filter cavity. A gas mixture is introduced into the annular cavities to control the velocity of sound within the cavities and the composition of the gas is controlled such that cavity resonance occurs at each pressure mode of interest. Various measurements are facilitated by the system such as slowly varying the composition of the gas and processing the microphone signals to directly obtain the modal amplitude distribution of a relatively time invariant sound field or adjusting the gas composition for cavity resonance at each mode of interest and recording transient phenomena of the acoustic energy propagating through the duct.

6 Claims, 11 Drawing Figures

APPARATUS FOR ANALYZING COMPLEX ACOUSTIC FIELDS WITHIN A DUCT

BACKGROUND OF THE INVENTION

This invention relates to the measurement of acoustic energy. More particularly, this invention relates to the measurement of acoustic energy propagating through a duct wherein the pressure pattern established by the acoustic energy is resolved into a number of component pressure patterns or modes.

It is known that a complex acoustic field can be resolved into a plurality of spatial wave components or modes which, when linearly combined, provide a substantially complete description of the acoustic field. Further, it is known that resolution of complex acoustic fields into such components is not only of value in understanding various phenomena associated with the propagation of acoustic energy, but is of great value in applied engineeing fields such as that branch of the acoustics arts which deals with sound attenuation or noise suppression. In particular, the resolution of complex sound fields into component pressure patterns often permits the artisan to design highly efficient sound suppressing apparatus for attenuating the associated sound energy or noise and further permits the artisan to reliably and precisely evaluate sound suppressing apparatus.

One example of a complex acoustic situation in which it is often desirable or necessary to resolve a generated sound field into component pressure patterns relates to acoustic energy propagating along a duct. In such a situation, not only do various duct parameters such as the cross-sectional geometry and the length of the duct affect the acoustic field, but further complications often arise in that the acoustic energy may originate from a variety of separate source, may encompass a relatively wide portion of the frequency spectrum, and may not be invariant or periodic with respect to time. One situation in which such conditions occur is the air inlet duct of a conventional gas turbine engine installation of the type utilized to propel aircraft.

Various noise sources are present in such an engine installation which generate acoustic energy that propagates generally forward through the air inlet duct. Such noise sources include, for example, noise originating because of the rotation of the rotor of an engine fan in the turbulent air which flows through the air inlet and the interactions between the rotors and stators of such a fan stage. Since acoustic energy travelling outwardly through such an air inlet represents significant portion of the noise generated by jet propelled aircraft, especially during takeoff and landing maneuvers, a great deal of effort has been expended to develop methods and apparatus for acoustically treating gas turbine engine air inlet ducts. To design highly efficient sound suppression systems for such inlet ducts, it is highly desirable to determine the characteristics of the sound field within the inlet so that the designer has detailed knowledge of the characteristics of the sound to be attenuated. Further, it is often advantageous to determine the characteristics of the sound field within a duct employing sound suppression equipment to thereby evaluate and possibly improve acoustic performance of the sound suppression equipment. Accordingly, acoustic studies of such inlet ducts are often undertaken.

One advantageous way of analyzing the complex acoustic field within a duct is the resolution of such a sound field into various sets of relatively simple pressure patterns or modes such as those sets of pressure patterns commonly called spinning modes and either axial modes or radial modes. For example, spinning modes are a series of pressure patterns along a periphery of the duct lying in a plane substantially orthogonal to the axial centerline and can be represented by the expression:

$$p = \Sigma_m p_m e^{im\theta} e^{i\omega t}$$

where m denotes the "mode number" that identifies each of the component pressure patterns and is equal to $\pm 1, \pm 2, \pm 3, \ldots, \pm m_c$ where $m_c$ is the highest order mode number which can propagate through the duct, pm is the amplitude constant of the "mth" order pressure pattern, $\theta$ is the angular coordinate relative to an axis of symmetry lying in a plane orthogonal to the duct, i is the imaginary operator, e is the base of the system of natural logarithms, and $\omega$ is equal to $2\pi f$, where f is the frequency of the acoustic signal within the duct that causes the acoustic field being analyzed.

Since $\theta$ ranges between zero and $2\pi$ radians, it can be realized that each spinning mode, i.e., the pressure pattern represented by the above stated equation for each particular value of m, can be thought of as a periodic spatial pattern which is orthogonal to the duct axis and includes exactly m pressure minima (and maxima). As is evidenced by the time dependent term, each modal pressure distribution rotates or spins clockwise or counterclockwise with respect to time with the direction of such rotation being determined by the algebraic sign ("+" or "−") that is associated with the mode number m. Further, it is known that substantially stationary pressure patterns or standing waves can occur at a particular mode number due to the existence of equal amplitude pressure signals of the positive and negative values of that particular mode number. Considering the linear combination or summation expressed by the above mathematical expression in conjunction with a similar expression representing either the axial or radial pressure components and in conjunction with the acoustic frequencies which cause the pressure pattern yields a substantially complete representation of the acoustic conditions within a duct.

In general, a large number of spinning modes are simultaneously present in the complex acoustic field associated with a duct such as a gas turbine air inlet since modal pressure patterns can be present for each frequency component or bands of frequencies within the acoustic signal that propagates through the duct and since the dimensions of such a duct often permit the existence of mode numbers ranging as high as 40 or more.

Prior art apparatus for resolving an acoustic field into spinning modes requires either a large number of microphones or a fixed microphone and a movable microphone. Each of these prior art techniques presents disadvantages and drawbacks in that the microphones and the equipment to process the signals supplied by the microphones generally require relatively complex calibration procedures. Further, with respect to apparatus employing a movable microphone, precise placement of the movable microphone must be effected for each measurement and use of such apparatus is limited to sound fields which do not vary with respect to time. Even further, these prior art procedures often require a great deal of time in order to gather measurements sufficient to allow resolution of the sound field into modal components. Once this information is gathered, such prior art systems often require fairly complex signal processing techniques to derive the modal components. Additionally, the prior art techniques often require the placement of acoustic detectors or microphones directly in the sound field under study or require a relatively large number of acoustic couplers to maintain the microphones in acoustic communication with the duct. In such systems, the microphones or acoustic couplers can alter the sound field within the duct and cause erroneous results.

Accordingly, it is an object of this invention to provide a system in which the complex pressure field that results from acoustic energy propagating through a duct can readily be resolved into modal components.

It is another object of this invention to provide a system for analyzing the sound field associated with the duct wherein neither a large number of microphones nor a movable microphone is required.

It is yet another object of this invention to provide a sound measurement system for determining the modal components of a sound field associated with the duct wherein the measurement system does not substantially alter the acoustic field being studied.

Even further, it is an object of this invention to provide a system for analyzing a complex sound field which results from acoustic energy propagating through a duct wherein the modal components of such sound field can be determined without extensive signal processing.

SUMMARY OF THE INVENTION

These and other objects are achieved in accordance with this invention by an acoustic measurement system which includes an acoustic filter that is acoustically coupled to the duct and selectively tuned such that the filter is excited into resonance by each modal component of the pressure pattern within the duct. Each disclosed filter includes one or more cavities that are tuned to each particular modal component of the duct pressure field by controlling the velocity of sound within the filter cavities. In this respect, the disclosed embodiments of the invention utilize two gas reservoirs which respectively contain a gas having a sonic velocity that exceeds that of air and a gas having a sonic velocity that is equal to or less than that of air wherein the two gasses are selectively mixed and supplied to the acoustic filter. When the gas mixture is controlled such that the sonic velocity within the filter cavities is related to the circumferential distance between nodes of the particular modal pressure pattern to which the filter is being tuned by a predetermined mathematical relationship, the filter resonates and maximum acoustic pressure is coupled through the acoustic filter.

The acoustic pressure within the acoustic filters of this invention is sensed by acoustic pressure detectors such as microphones that are coupled to the filter cavities. Since the filter cavities are dimensioned and arranged so that the transfer of acoustic pressure from the duct to the filter is substantially greater under resonant conditions than it is under non-resonant conditions, the acoustic detectors supply signals representative of the pressure constants associated with the modal component or mode order that excites the cavity into resonance.

A signal processor receives the signals supplied by the acoustic detectors and electronically processes the signals to determine the two amplitude constants that are respectively associated with the positive and negative values of the mode order that is exciting the filter into resonance, i.e., the mode order to which the acoustic filter is tuned.

Various measurements are facilitated with the acoustic measurement system of this invention. For example, in determining the mode structure of a relatively steady pressure field, i.e., a sound field within the duct that doesn't vary with time, the composition of the gas mixture is continuously varied and the signal processor supplies a signal which, when considered over the range of the gas composition, depicts the modal amplitude distribution of the pressure field within the duct. In situations in which the transient characteristics of the duct pressure pattern are to be determined, the gas mixture is stabilized at a sonic velocity which corresponds to each particular modal component, the duct is excited with the acoustic signal and the signal processor supplies a signal representative of the two amplitude constants as a function of time.

In one disclosed embodiment, wherein the duct which includes the acoustic pressure pattern that is to be resolved into modal components is cylindrical, the acoustic filter comprises a single annular cavity that is concentrically formed about an axial portion of the duct. In this embodiment, a series of circumferentially spaced apart openings in the duct are located along one of the radially extending boundary walls of the cavity to acoustically couple the duct to the cavity and two or more acoustic detectors that are circumferentially spaced apart from one another sense the acoustic pressure within the cavity.

In some situations, because of the duct dimensions and the frequency characteristics of the acoustic energy propagating within the duct, the sonic velocity of an available gas is not high enough to cause an acoustic filter to resonate at a first natural frequency in response to lower order modal components of the duct pressure pattern. In accordance with this invention, determination of the mode structure at such lower order modes is effected by dimensioning the cavity such that two modes of cavity resonance can occur, i.e., resonance can be effected both at a first and second natural frequency. In such an embodiment of the invention, the cavity is dimensioned such that resonance at a first natural frequency is utilized for the determination of the higher order modal components and resonance at a second natural frequency is utilized for the determination of lower order of modal components.

In one such arrangement of the invention, the axial length of the filter cavity is dimensioned such that each gas mixture required to excite resonance at a second natural cavity frequency to determine the lower order pressure modes has a sonic velocity less than that of air wherein the corresponding first natural frequency of cavity resonance lies beyond the cutoff mode of the duct. Accordingly, signals are not induced into the cavity which would otherwise interfere with the determination of the lower order modal components.

In accordance with the invention, lower order pressure modes can also be determined by the use of a single cavity wherein the cavity radial dimension is established to cause the cavity to resonate at a second natural frequency. In such an embodiment of the invention, the resonance at the second natural frequencies of the filter cavity which correspond to the lower order modal components is effected by a gas mixture having a sonic velocity that substantially exceeds of air. Greater modal resolution is generally achieved with this type of cavity than is achieved with the previously described cavity that resonates at a second natural frequency when supplied with the gas having a sonic velocity less than air.

In another disclosed embodiment of the invention, the acoustic filter includes three annular cavities which circumferentially surround the duct. This embodiment includes a cavity of the above-described type which is dimensioned for resonance at a first natural frequency for resolving higher order duct pressure modes, a second cavity of the above described type that is dimensioned for resonance at a second natural frequency for resolving lower order duct pressure modes with a gas mixture which has a sonic velocity exceeding that of air, and a third annular cavity which is dimensioned and arranged to effectively serve as a blocking filter that prevents higher order modes that excite the second cavity into resonance from reaching the acoustic detectors. In this arrangement, two series of circumferentially spaced apart openings respectively couple the duct to the first and second cavities and a third series of circumferentially spaced apart openings, located in a common boundary wall between the second and third cavities, acoustically couple the third cavity to the second cavity. Acoustic detectors, mounted in the first and third cavities, respectively supply signals representative of the pressure amplitude at each of the lower and higher modal components as the composition of the gas within the first and second cavities is varied or controlled. Generally, the third cavity is filled with the gas having a relatively low sonic velocity to achieve the desired filtering characteristics.

BRIEF DESCRIPTION OF THE DRAWINGS

Other objects and advantages of the present invention will become apparent to one skilled in the art after reading the following description, taken together with the accompanying drawing, in which.

DETAILED DESCRIPTION

Figures 1, 2:
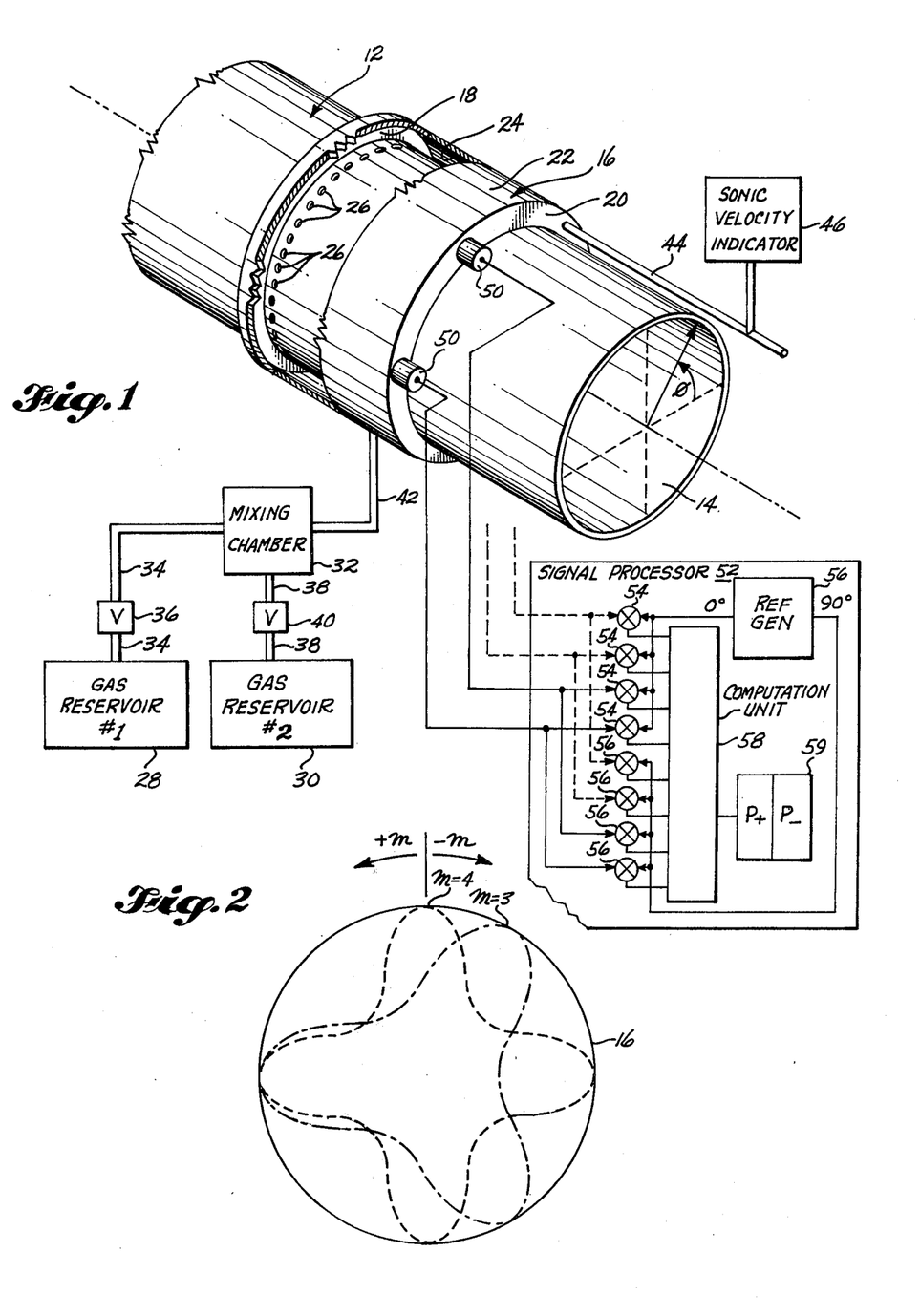
FIG. 1 pictorially represents an acoustic measurement system in accordance with this invention for resolving the acoustic pressure pattern within a circular duct into those modal components commonly referred to as spinning modes.
FIG. 2 depicts two pressure patterns within a duct that correspond to spinning modes of the orders 3 and 4.

In the acoustic measurement system depicted in FIG. 1, a circular duct 12 carries acoustic energy which is assumed to be propagating generally outwardly through an exit opening 14. In the situations to which this invention is primarily addressed, the acoustic energy that propagates through the duct 12 cannot be considered a simple planar or spherical wave that travels axially along the duct 12, but is generally a relatively complex time varying pressure pattern which includes various frequency components that are generated by a number of acoustic sources. Those skilled in the art will recognize that many situations of this type are encountered. Thus, although the invention is described herein relative to the acoustic field generated within the air inlet of a gas turbine engine installation, it will be recognized that the invention is applicable to a wide variety of situations including, but not limited to, the intake and exhaust ducts of gas turbine engines.

For example, considering an application of the invention wherein the duct 12 is the air inlet duct of the gas turbine engine installation of the type utilized to propel aircraft, a variety of acoustic sources generates signals which propagate against the direction of airflow and hence pass outwardly through the entrance opening 14 of the duct 12. The gas turbine engine of such an engine installation includes a number of sources of acoustic energy varying both in frequency content and in the direction in which the acoustic signals are radiated. For example, the operation of the fan stage of a gas turbine engine of the turbofan type in itself causes generation of a variety of acoustic signals due to the rotation of the rotor assembly and interaction of the rotors and stators with the turbulent airflow within the air inlet.

Since the acoustic signals generated by the fan stage and by other components of the gas turbine engine involve a number of signal components having various frequency characteristics wherein the acoustic signals have radial, axial and circumferential components of particle velocity, the sound energy does not simply propagate axially along the inlet duct, but these signals interact with the boundaries of the inlet duct to establish a complex acoustic pattern within the inlet duct. For example, because of such interaction, certain components of the acoustic energy propagating through the duct effectively follow a helical or spiral path along the duct wall prior to emerging from the duct opening 14. As previously noted, such acoustic components can be considered as a linear combination of relatively simple pressure patterns or modes, with knowledge of the frequency of the acoustic signals causing the pressure patterns and knowledge of two modal distributions that are referenced to two coordinate directions providing a substantially complete description of the complex pressure field within the duct. In this respect, a linear combination of what is commonly called the "spinning modes" is often utilized with a linear combination of modal components taken along either the axial or radial direction.

FIG. 2, which illustrates the duct 12 in cross section, demonstrates unit spatial pressure patterns that are associated with the spinning modes of the acoustic pressure field within the duct 12. In general, the "mth" order spinning mode corresponds to a symmetric pressure pattern around the periphery of the duct 12 which includes exactly m pressure maxima and minima. For example, FIG. 2 illustrates the third and fourth order spinning modes which respectively include three and four pressure maxima (and minima) wherein the circumferential distance between adjacent pressure maxima (or minima) is equal to the diameter of the duct 12 divided by the mode order. As is indicated by the arrows in FIG. 2, the spatial pressure pattern associated with each mode order is not necessarily stationary with respect to time, but spins or rotates within the duct. In this respect, each modal component can exhibit a value for both positive and negative values of the particular mode order, m, with the positive and negative values being associated with opposite directions of rotation. Thus, depending on the relative amplitudes associated with the positive and negative values of a particular mode order, the pressure pattern associated with that particular mode may rotate in either direction, or if the amplitudes of the positive and negative values of the mode order are substantially equal, a "standing wave" is established which is substantially stationary in space.

Referring again to FIG. 1, the acoustic measurement system of this invention includes an acoustic filter (generally denoted by the numeral 16) which coaxially encompasses the duct 12. The acoustic filter 16 of FIG. 1, which is further illustrated in FIG. 3, includes two spaced apart radially extending walls 18 and 20 and an axially extending cylindrical wall 22 that is joined to the walls 18 and 20 so as to form a substantially closed annular cavity 24. A series of small openings 26 acoustically couple the duct 12 to the cavity 24 with the openings 26 being circumferentially spaced apart from one another.

Figure 3:
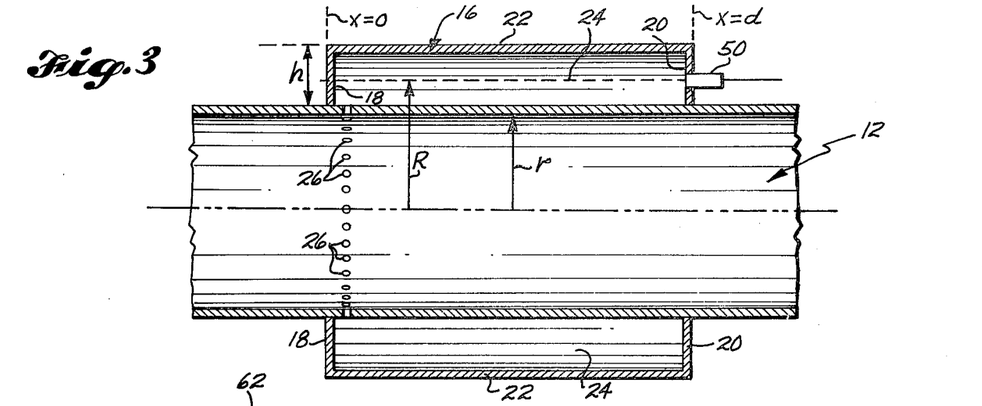
FIG. 3 is a cross-sectional view of the acoustic filter of the acoustic measurement system depicted in FIG. 1 wherein the acoustic filter includes a single annular cavity.

To prevent the cavity 24 from substantially altering the acoustic pressure pattern within the duct 12 and, as shall be described in more detail hereinafter, to increase the modal resolution of the acoustic filter 16, the openings 26 are dimensioned and arranged to exhibit a relatively high acoustic impedance. Further, to prevent or impede fluid flow between the duct 12 and the cavity 24, the openings 26 are dimensioned and arranged to exhibit a relatively high resistance to fluid flow. A variety of openings which satisfy these constraints can be realized. For example, a large number of circular holes or elongate slits that are covered with a thin flexible membrane or filled with a porous material having a high acoustic resistance can be utilized. Further, a relatively large number of relatively small openings that are not covered with a flexible membrane or filled with a porous material are generally satisfactory and, due to increased sensitivity to the pressure pattern within the duct 12, may often be preferred over other suitable openings. Such openings are dimensioned so that the percentage open area, i.e., the ratio of the total open area of the openings 26 to the cross-sectional area of the cavity 24, is substantially less than 1 percent. Utilizing this percentage open area, it has been found that, since the pressure difference between the cavity 24 and the interior of the duct 12 is generally not substantial, a significant amount of fluid does not flow through the openings 24. This is especially true of situations such as the previously mentioned air inlet ducts wherein air is flowing through the duct 12 and, in the absence of a substantially higher fluid pressure within the cavity 24, inhibits the gas within the cavity 24 from flowing inwardly into the duct 12.

Regardless of the exact configuration of the openings 26, the cavity 24 is dimensioned and arranged so that the cavity 24 can be tuned to resonate at a pressure distribution which corresponds to the pressure pattern of each of the spinning modes by controlling the composition of the gas within the cavity 24. More specifically, in accordance with this invention, the cavity 24 exhibits resonance at one or more natural frequencies which are determined by the physical dimensions of the cavity 24 and the velocity of sound within the cavity. More specifically, and as shall be described in more detail hereinafter, the cavity 24 is dimensioned such that the pressure pattern associated with each spinning mode excites the cavity into resonance when the sonic velocity of the gas within the cavity 24 is related to the circumferential distance between adjacent nodes of the pressure pattern associated with a selected spinning mode by a predetermined mathematical relationship.

To supply the cavity 24 with the gas having a controllable sonic velocity and thereby permit the acoustic filter 16 to be selectively tuned to each spinning mode, the embodiment of the invention depicted in FIG. 1 includes two gas reservoirs 28 and 30 which are respectively interconnected to a mixing chamber 32 via a fluid conduit 34 and valve 36 and a fluid conduit 38 and associated valve 40. Generally, the reservoirs 28 and 30 are pressure vessels which contain a supply of the gasses to be utilized either in a highly compressed or liquid state. Valves 36 and 40 are conventional components which are adjustable to control the rate at which the two gasses enter the mixing chamber 32. Mixing chamber 32 is a conventional component such as a manifold which permits or induces mixing of the two gasses prior to coupling the gas mixture to the cavity 24 via the fluid conduit 42.

Preferably, the acoustic filter 16 includes a second fluid conduit 44 which permits gas to be exhausted from the cavity 24 during periods of time in which an additional quantity of gas is entering the cavity 24 via the fluid conduit 42 and thereby maintain the pressure within the cavity 24 substantially equal to the atmospheric pressure. In situations in which the interior of duct 12 is of less atmospheric pressure, reduced fluid flow through the openings 26 can be achieved by decreasing the fluid pressure within the cavity 24. For example, a conventional evacuation pump (not shown in FIG. 1) can be connected to the fluid conduit 44.

In the system of FIG. 1, a sonic velocity indicator 46 is depicted in fluid communication with the fluid conduit 44 for determining the speed of sound within the cavity 24. A variety of devices for determining the speed of sound within a gas are known, including devices which are responsive to the composition of the gas and devices which involve a determination of the time required for an acoustic signal at a relatively stable frequency to propagate over a known distance. Further, although the sonic velocity indicator 46 is shown in FIG. 1 as being coupled to the fluid conduit 44, such a device can be coupled to the fluid conduit 42 or, in many situations, it is preferably mounted and contained within the cavity 24 of the acoustic filter 16. Regardless of the exact configuration of the sonic velocity indicator 46 and its physical location within the system of FIG. 1, the indicator 46 permits control of the composition of the gas mixture within the cavity 24 such that the cavity 24 can be tuned to resonate at each of the spinning modes.

To sense the acoustic pressure that is coupled into the filter cavity 24, the acoustic filter 16 includes two or more acoustic detectors such as piezoelectric or condenser type microphones which are circumferentially spaced apart from one another along the boundary wall 20 of the cavity 24. Each acoustic detector 50 supplies a signal representative of the acoustic pressure along the boundary wall 20 at the position at which that particular acoustic detector is mounted. As shall be described in detail hereinafter, at least two acoustic detectors 50 are required in order to separate the acoustic pressure that is detected at each of the spinning modes into component amplitude factors that are respectively associated with the positive and negative values of that mode order. Further, and as shall be described in more detail hereinafter, more than two microphones are preferably employed with the microphones being spaced apart from one another by unequal spacings over a segmented portion of the boundary wall 20. Such spacing eliminates measurement errors which could result when standing waves are present in the duct 12 without the necessity of providing a movable microphone.

Regardless of the number of acoustic detectors employed, each of the acoustic detectors 50 supply an electrical signal to a signal processor 52. The signal processor 52 includes circuitry for combining the signals supplied by the acoustic detectors 50 to determine the amplitude of the two pressure constants that are associated with the positive and negative modal components at the mode order currently being determined. As shall be described in more detail hereinafter, the signal processor 52 can include a variety of conventional circuit arrangements which are effectively responsive to the signals provided by the acoustic detectors 50 and the relative phase angle of such signals.

The dimensioning of the acoustic filter 16 of FIGS. 1 and 3 can best be understood by examining the theoretical considerations that form the basis of the operation of this invention. For simplicity, such analysis can be carried out by disregarding the curvature of the cavity, (i.e., by assuming that h is much less than R where, as noted in FIG. 3, h is the radial dimension of the cavity 24 and R is the mean radius of the cavity 24) and by assuming that the cavity is excited along the cavity wall 18. If the openings 26 exhibit an acoustic impedance which is large enough to prevent pressure perturbations in the pressure distribution along the duct wall, the duct wall pressure pattern can be expressed as:

$$p' = \Sigma_m p'_m e^{im\theta} e^{i\omega t}$$

where p' is the pressure along the duct wall at a radial position $\theta$, m is the order of each of each spinning mode of interest, $p'_m$ is the amplitude constant of the "mth" modal component, i is the imaginery operator, $\omega$ is $2\pi f$ where f is the frequency of the acoustic signal propagating within the duct, and t is the time variable.

With the openings 26 coupling this pressure field into the cavity 24, it can be shown that the acoustic pressure within the cavity 24 is:

$$p = \Sigma_m p_m \cos ax \, e^{im\theta} e^{i\omega t}$$

where $p_m$ is an amplitude constant associated with the mth duct mode, x is the distance between the cavity wall 18 and the point of interest (FIG. 3), a is given by the expression $a^2 = k^2 - (m/R)^2$ where R is the mean radius of the cavity 24 (i.e., R is equal to the radius r of the duct 12 added to h/2) and the wave number k is equal to $\omega/c_c$ and $c_c$ is the velocity of sound within the cavity 24.

Since the particle velocity u at the cavity wall 20, (i.e., x = d) is given by the expression $dp/dx = -i\rho\omega u$, where $\rho$ is the density of the gas in the cavity 24, the relationship between the pressure p at the cavity wall 20 and the pressure p' at the cavity wall 18 can be shown to be p − p' = Zu, where Z is the acoustic impedance of the openings 26 and u is the average particle velocity along the boundary wall 20.

Since this relationship must hold for each mode order ± m of the pressure pattern within the duct 2, it can be shown that the transfer function, (i.e., $p'_{m/p_m}$) which relates the modal pressure $p'_m$ at the cavity wall 18 to the modal pressure $p_m$ at the cavity wall 20 is:

$$T = 1/[\cos ad - (Za/ik\, C_c) \sin ad] \quad (1)$$

Although inclusions of effects such as cavity damping and response time requires a numerical computation of the transfer function T for a particular cavity design, the more important characteristics of the cavity, and hence, approximate design criteria can be determined by suitable approximations. Specifically, sinc Z necessarily includes a substantial real part, it can be seen that maximizing T to maximize the pressure coupled to the microphones 50 requires that the $(Za/ik\rho c_c)$ sin ad in Equation 1 be minimized. In this respect, it can be noted that this term becomes identically equal to zero such that T becomes equal to unity whenever ad = 0, $\pi$, $2\pi$, $3\pi$, . . . Thus it can be recognized that the cavity 24 exhibts resonance at a series of natural frequencies (i.e., multiple mode resonance) determined by the expression ad = $n\pi$, where n = 0, 1, 2, 3, . . . Utilizing the previously mentioned expression for a, it can thus be shown that the cavity resonates when the velocity of sound within the cavity 24 is:

$$c_c = dR \, (n^2\pi^2 R^2 + d^2 m^2)^{-\frac{1}{2}} \quad (2)$$

Accordingly, it should be noted that by suitably selecting the cavity dimensions d and h, and by controlling the velocity of sound within the cavity 24, the acoustic filter 16 of FIGS. 1 and 3 can be caused to resonate at each duct mode m of interest. In this respect, considering the first natural frequency of cavity resonance, i.e., n = 0, it can be observed that the cavity 24 resonates at such first natural frequencies whenever the sonic velocity within the cavity 24, $c_c$ is equal to $R\omega/m$.

Several things can be noted about cavity resonance at such first natural frequencies. Firstly, it can be noted that n is equal to zero only when a is equal to zero (i.e., $\omega/c_c = m/R$). Thus, with reference to Equation 1, it can be observed that both the "sin ad" term and the coefficient term of this expression are identically equal to 0 when the cavity 24 resonates at a first natural frequency. Accordingly, if the cavity 24 is dimensioned to resonate at a first natural frequency for each mode order of the duct spinning modes as the sonic velocity of the gas within the cavity 24 is controlled, rather sharp resonant characteristics are effected with the transfer function T becoming equal to unity under resonant conditions and being of the order 1/Z for off-resonant conditions.

Secondly, it can be noted that the distance between adjacent maxima of the pressure pattern which corresponds to each mode order m is equal to $2\pi r/m$ and that the wavelength of the signal within the cavity 24 when the cavity resonates at a first natural frequency is equal to $2\pi R/m$, which is equal to $2\pi r/m + \pi h/m$. Thus, when the cavity 24 resonates at a first natural frequency, the wavelength of the signal within the cavity 24 is mathematically related to the circumferential distance between nodes of the duct pressure pattern which corresponds to the mode order m.

With respect to utilizing the first natural frequencies of resonance for resolving the pressure field within the duct into modal components, it should be noted that, depending on the frequency of the acoustic signal (W) within the duct 12 and the radial dimension of the apparatus (R), measurement of low mode orders require a gas mixture having rather high sonic velocity. In fact, in applications such as the resolution of acoustic pressure patterns of a gas turbine air inlet duct into various spinning modes, the frequencies of interest are generally in the range of 1,000 to 5,000 Hz and the radius of the duct is often in the range of 0.5 to 1.3 meters. Thus, considering, for example, a frequency of 2,500 Hz and an R dimension of 1 meter, it can be seen that a sonic velocity in excess of 1,500 meters per second is required to determine the pressure component at mode order 10. A gas having such a sonic velocity at a moderate temperature is not known.

In accordance with this invention, this limitation is averted by dimensioning the cavity 24 so that resonance can occur at both first and second natural frequencies of cavity resonance. In particular, in accordance with this invention, the cavity 24 is dimensioned such that lower order duct modes which cannot be resolved when the cavity 24 resonates at a first natural frequency (because of inherent constraints in the velocity of sound within available gasses) are resolved with the cavity 24 resonating at one of the other natural frequencies and the higher order duct modes are resolved with the cavity 24 resonating at a first natural frequency. In this respect, the cavity 24 is preferably dimensioned and arranged such that resonance at a second natural frequency (i.e., n equal to unity in Equation 2) is utilized to resolve the mode components at such "lower" order duct modes.

Such a partitioning of the spinning mode orders into a range of lower modal orders and a range of higher modal orders that are respectively resolved with the cavity 24 resonating at a second natural frequency and resonating at a first natural frequency can be effected by dimensioning the cavity 24 in two specific manners. As shall be described in more detail hereinafter, applying a first set of dimensional constraints to the cavity 24 causes the cavity to resonate at a second natural frequency when the sonic velocity of the gas mixture within the cavity 24 is lower than that of the gas within the duct 12 (which gas has, for the purposes of this disclosure, been assumed to be air) and causes the cavity 24 to resonate at a first natural frequency when the sonic velocity within the cavity 24 exceeds that of the gas within the duct 12. In these embodiments of the invention, the cavity 24 is dimensioned such that the first natural frequencies which correspond to the second natural frequencies that are utilized to resolve lower order duct modes lie beyond the maximum spinning mode that can be sustained within the duct 12, i.e., are greater than the duct cutoff mode. Thus, as the composition of the gas mixture is controlled and the cavity 24 resonates at a second natural frequency for resolving the lower order duct modes, signals are not induced into the cavity which could cause resonance at a first natural frequency. Accordingly, extraneous signals are not induced into the cavity 24 of such an embodiment of the invention during the determination of lower order mode components and additional signal filtering is not generally required.

The embodiments of this invention which utilize a filter cavity dimensioned to achieve the above-described mode of operation can best be understood by recognizing that duct spinning modes of an order greater than a specific integer, which is commonly denoted as the duct cutoff mode, will not propagate along the duct but will be exponentially attenuated if introduced therein. For example, with respect to the circular duct of FIG. 1, it is known in the art that the previously described parameter a must be a real number for each particular spinning mode that propagates along the duct length. Hence, utilizing the previously mentioned mathematical expression for the parameter a, it can be shown that the duct cutoff mode is the largest integer which is less than or equal to $\omega r/c_d$ where $c_d$ is a sonic velocity within the gas that is contained within the duct 12.

Utilizing Equation 2 and applying the constraint that the sonic velocity of the gas mixture which causes the cavity 24 to resonate at the highest duct mode order that is to be resolved with the cavity resonating at a second natural frequency must be less than the sonic velocity which causes the cavity 24 to resonate at a first natural frequency when the pressure component at the cutoff mode is determined, it can be shown that the cavity 24 must be dimensioned such that:

$$d/R < \pi/(n_c^2 - n^2)^{1/2} \qquad (3)$$

where $n_c$ is the order of the cutoff mode and n is the highest order mode that is to be determined with the cavity resonating at a second natural frequency. Since, as shall be described hereinafter, the modal resolution achieved with such an acoustic filter embodiment resonating at a first natural frequency is substantially superior to that effected with the filter resonating at a second natural frequency, the duct order n is normally established at the lowest possible value, i.e., n is normally the highest order duct mode which is less than $\omega R/c$ where c is the maximum sonic velocity achievable within an available gas. Since, the embodiments of the invention having the cavity 24 dimensioned in the previously described manner are constrained with an upper limit upon the ratio d/R, such filter cavities are, for convenience of description, referred to hereinafter as "shallow cavities".

Figure 4A:
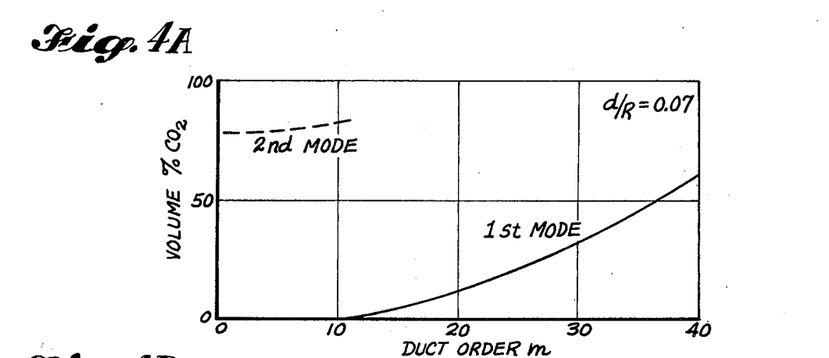
FIGS. 4a and 4b graphically depict typical characteristics of realizations of the acoustic filter of FIG. 3 in which the filter cavity is dimensioned for resonance at two natural frequencies with a first natural frequency being utilized for the resolution of each higher order duct mode and a second natural frequency being utilized for resolution of each lower order duct mode wherein cavity resonance at each of the lower order duct modes is effected by a gas mixture having a sonic velocity less than that of air.
Figure 4B:
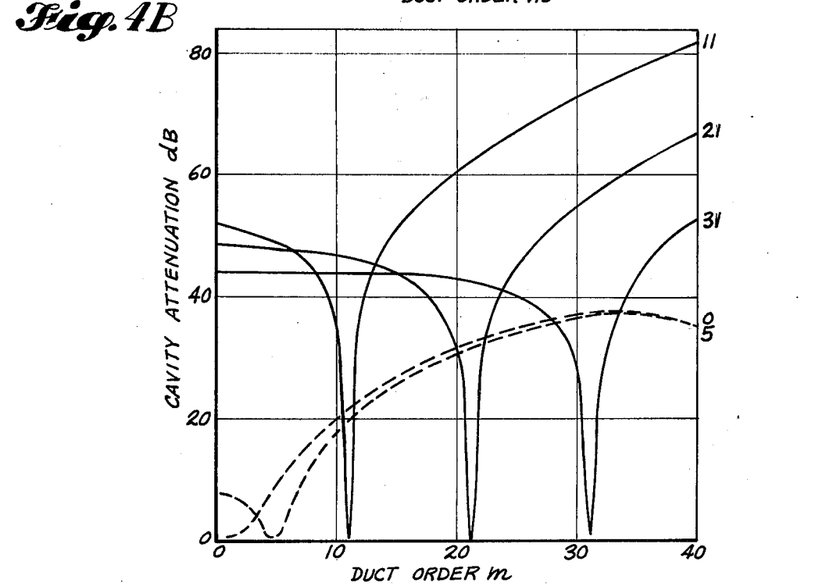

FIG. 4 depicts typical performance characteristics of a realization of the invention which utilizes a single shallow cavity as the acoustic filter 16. In the situation depicted in FIG. 4, carbon dioxide ($CO_2$) is mixed with hydrogen ($H_2$) to provide a gas mixture which can be controlled such that the sonic velocity of various compositions of the gas mixture ranges between that of pure $H_2$ (approximately 1330 meters per second at 20 degrees Celsius) to less than that of air (approximately 343 meters per second at 20 degrees Celsius). Further, as is indicated in FIG. 4, the radius of the duct 12 is such that the cutoff mode is of order 40 and the frequency of the acoustic energy propagating along the duct and the duct radius are such that $\omega R/c$ is substantially unity at mode order 11 when the cavity is filled with pure $H_2$. Thus, by utilizing the dimensional constraints of Equation 3, it can be seen that, in this particular situation, the ratio of the duct length d to the mean radius R of the cavity 24 (d/R) must be less than $0.1\pi/\sqrt{15}$, which is approximately equal to 0.08. As is indicated in FIG. 4a, the value of the ratio d/R that is utilized in the embodiment of the invention which provides the depicted operating characteristics is 0.07, a value of which satisfies the above constraint.

Viewing FIG. 4a, it can be seen that this shallow cavity embodiment is selectively tuned to resonate at a series of first natural frequencies which correspond to each spinning mode of order 11–40 (the cutoff mode) as the percentage volume of $CO_2$ in the $CO_2$ — $H_2$ mixture is increased from zero to approximately 60 percent, i.e., as the velocity of sound of the gas mixture that fills the cavity 24 is controlled between that of pure hydrogen and a sonic velocity slightly less than that of air with the sonic velocity required to tune the cavity to each particular mode order m being given by the expression $c_c = \omega R/m$. When the percentage of $CO_2$ is increased above that which excites resonance at a first natural cavity frequency in response to the modal component at the duct cutoff mode (40), i.e., the sonic velocity of the gas within the cavity is further reduced, the cavity is selectively tuned to resonate at a series of second natural frequencies which correspond to the mode orders 1–10. In particular, the sonic velocity which causes each of the mode order 1–10 to excite the cavity into resonance at a second natural frequency is given by utilizing a value of unity for the parameter n in Equation 2.

Figure 6A:
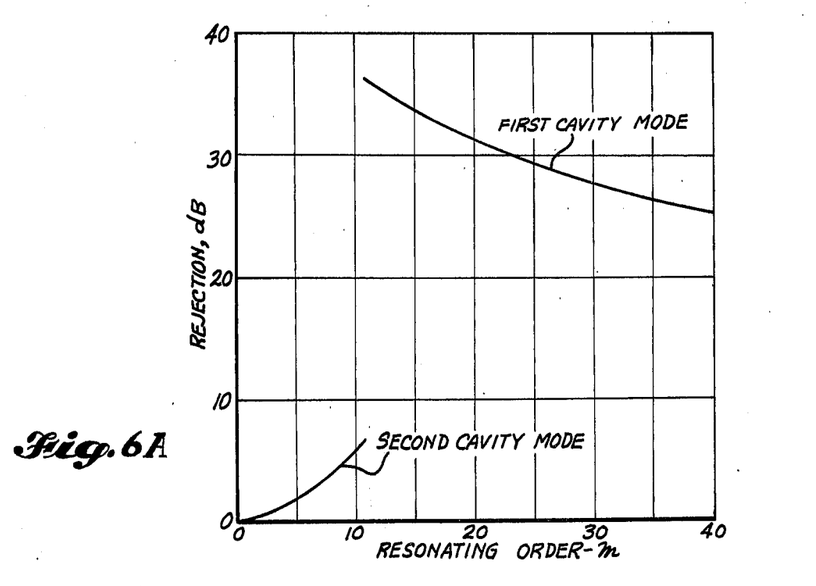
FIGS. 6a and 6b graphically depict the resolution between adjacent duct modes that is typically effected with arrangements of the invention which have the characteristics depicted in FIGS. 4 and 5.

FIG. 4b depicts the pressure transfer characteristics of Equation 1 for the above-described realization of such a shallow cavity embodiment of the invention for mode numbers 0, 5, 11, 21 and 31. As can be seen in FIG. 4b, the filter characteristics of such an embodiment of the invention are relatively sharp when the cavity is caused to resonate at a first natural frequency to resolve the modal components at the higher order spinning modes (depicted mode orders 11, 21 and 31), but are less sharp when the cavity is caused to resonate at a second natural frequency to resolve modal components at the lower order spinning modes (e.g., mode orders 0 and 5 in FIG. 4b). With reference to FIG. 6a, which depicts the amount of resolution (rejection in dB), between adjacent mode orders for the above-described shallow cavity realization of the invention, it can be realized that dimensioning the cavity 24 to resonate at a second natural frequency that corresponds to lower spinning mode orders when the cavity 24 is filled with a gas having a sonic velocity lower than that of air, may not be satisfactory in all situations. In particular, as is indicated in FIG. 4b and as is most clearly depicted in FIG. 6a, when the invention utilizes the above-described shallow cavity in the acoustic filter 16, and is tuned for resonance which corresponds to one of the higher duct modes, all other duct modes are rejected or attenuated by at least 25 dB. On the other hand, the rejection or attenuation effected when the cavity is tuned to resonate at a second natural frequency to determine the pressure component at a lower order spinning mode is less than 10 dB and decreases as the duct order of interest decreases.

In situations in which it is desirable or necessary to attain greater resolution of the lower order duct modes, the acoustic filter 16 can be dimensioned and arranged to include a "deep cavity" instead of, or in addition to, the above described shallow cavity. Like the term shallow cavity, the term deep cavity is utilized hereinafter for simplicity in terminology and, for the purposes of this disclosure, denotes a cavity having a d/R ratio which exceeds that set forth in Equation 3.

Like the above-described shallow cavity embodiments of the invention, the deep cavity embodiments of this invention are dimensioned and arranged for the determination of lower order modal components of the pressure field within the duct (i.e., those modal components which cannot be resolved with the cavity operating at a first natural frequency because of inherent limitations in the sonic velocity of the gasses) with the cavity resonating at a second natural frequency. Further, and in contrast with the previously described shallow cavity embodiments, the deep cavity embodiments of the invention are dimensioned such that the cavity selectively resonates at a second natural frequency in response to each of the lower spinning mode orders when the cavity is filled with the gas mixture having a sonic velocity which exceeds that of the gas within the duct 12, i.e., a sonic velocity which exceeds the sonic velocity of air.

In particular, considering Equation 2, it can be seen that for resonance to be induced in the cavity 24 at a second natural frequency when the mode order is 0, the required sonic velocity of the gas mixture within the cavity 24 is $d\omega/\pi$. Further, from Equation 2, it can be seen that resonance at a series of second natural frequencies that correspond to each modal component of order greater than 0 can be attained by adjusting the gas mixture to exhibit a lower sonic velocity. Accordingly, when a deep cavity embodiment of the invention is dimensioned so that $d\omega/\pi$ is equal to or less than the sonic velocity of an available gas, e.g., Hydrogen, cavity excitation at a second natural frequency which corresponds to each of the lower order modal components of the duct pressure pattern can be achieved.

Figure 5A:
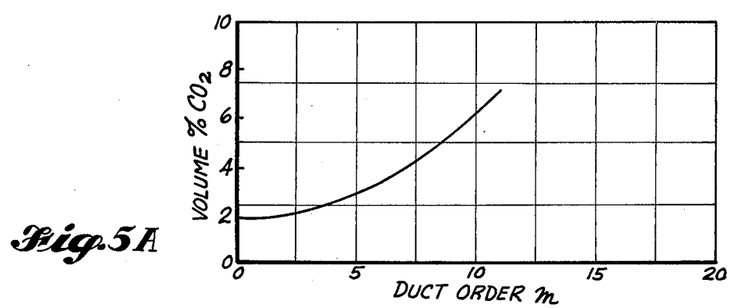
FIGS. 5a and 5b graphically depict typical characteristics of realizations of the acoustic filter of FIG. 3 in which the filter cavity is dimensioned for resonance at two natural frequencies with resonance at a second natural frequency being utilized for resolution of each lower order duct mode wherein cavity resonance at each of the lower order duct modes is effected by a gas mixture having a sonic velocity greater than that of air.
Figure 5B:
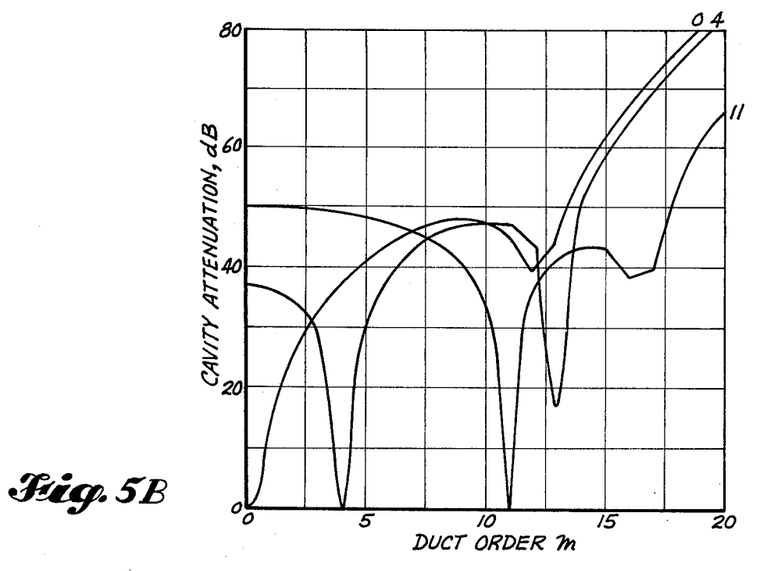

The above described design considerations and other performance characteristics of a "deep cavity" embodiment of this invention are illustrated by FIGS. 5a and 5b. Specifically, FIGS. 5a and 5b depict the characteristics of a realization of a deep cavity embodiment of the invention which is dimensioned for operation in the previously described situation in which the frequency of the acoustic signal ($\omega$) within the duct 12 and the radial dimension of the cavity 24 (R) prevents the cavity 24 from being excited into resonance at a mode order of 10 or less due to inherent limitations in the sonic velocity of the known gasses. In the realization of the deep cavity embodiment which resulted in the performance characteristics depicted in FIGS. 5a and 5b, the duct cutoff mode is of order 40 and the cavity d/R ratio is established at 0.25 and hence exceeds the inequality setforth in equation 3 which describes the shallow cavity and deep cavity embodiments of the invention. Further, as depicted in FIG. 5a, the duct dimension d of the realization of the deep cavity embodiment which resulted in the depicted performance characteristics is selected such that the sonic velocity of a $H_2$ — $CO_2$ gas mixture which includes approximately 2% $CO_2$ by volume is equal to $d\omega/\pi$.

Viewing FIG. 5a, in the above-described realization of a deep cavity embodiment of the invention, the acoustic filter 16 is selectively tuned to the lower order modes by controlling the $H_2$ — $CO_2$ gas mixture over a range which includes between 2% and approximately 6% $CO_2$ by volume. In this respect, the sonic velocity necessary to excite cavity resonance at a second natural frequency which corresponds to each modal component of order one through ten is given by utilizing the selected values of d and R and a value of n equal to unity in Equation 2.

Viewing FIG. 5b, which depicts the pressure transfer characteristics of Equation 1 or the above-described deep cavity embodiment of the invention, and comparing these characteristics with those of the shallow cavity embodiment that are depicted in FIG. 4b, it can be seen that much sharper filter characteristics and hence greater modal resolution is attained in a deep cavity embodiment which is excited into resonance at a second natural frequency when the cavity is filled with a gas mixture having a relatively high sonic velocity. In particular, it can be observed in FIG. 5b that the transfer characteristics of the lower order modes (0 and 4) of such a deep cavity embodiment are comparable to the transfer characteristics obtained at higher order duct modes (e.g., the depicted mode order 11) in which the cavity is excited into resonance at a first natural frequency. As can also be ascertained from FIG. 5b, in such a deep cavity embodiment, the gas mixture which causes the cavity to resonate at a second natural frequency for determining a modal component at a lower order mode can also cause the cavity to be excited into resonance at a first natural frequency in response to a higher order duct mode. In this respect, it can be shown from Equation 2 that a gas mixture which tunes a deep cavity embodiment of the invention to resonate at a second natural frequency in response to a lower order duct mode $m_1$ will also cause resonance at a first natural frequency for higher order modal component of an order equal to $(\pi^2 R^2/d^2 + m_1^2)^{\frac{1}{2}}$. Thus, if duct modes are present at or near such a value, additional acoustic energy can be coupled into and through filter embodiments which utilize a deep cavity.

Figure 6B:
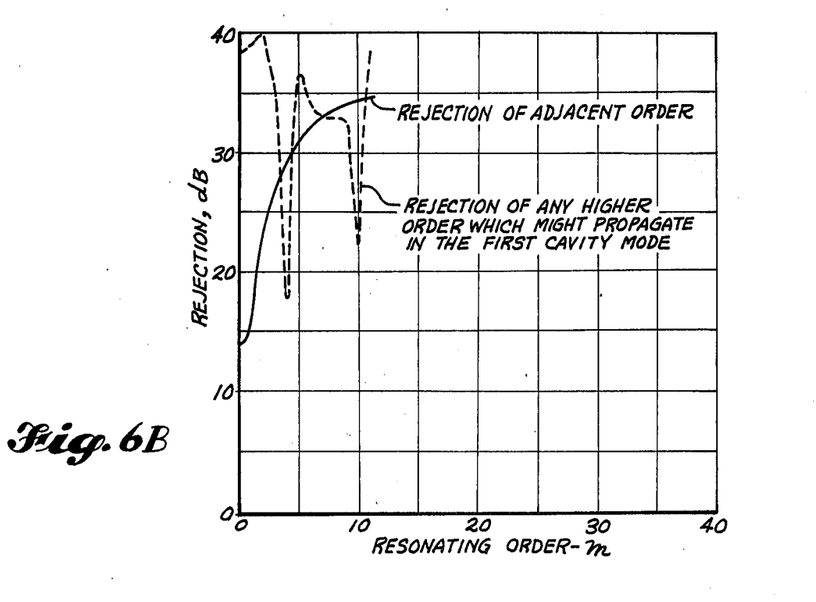

For example, with reference to FIG. 5b, the gas mixture which causes the above-described deep cavity embodiment to resonate at a second natural frequency for determining the modal component of order 4 also causes that particular deep cavity to resonate at a first natural frequency which nearly corresponds to mode order 13. As is shown in FIG. 5b, the pressure transfer characteristic exhibited when such a cavity is tuned to resonate in response to the fourth order modal component provides approximately 30 dB of attenuation at the next highest mode order (5) with the attenuation increasing to approximately 48 dB at mode order 10, decreasing to approximately 18 dB at mode order 13 and rapidly increasing again for mode orders greater than 13. This relationship is also clearly set forth in FIG. 6b wherein the solid line depicts the cavity rejection or attenuation of acoustic energy associated with duct modes adjacent to the modal component to which the cavity is tuned and the broken line depicts the relative amount of acoustic energy which can be coupled into the cavity 24 by simultaneous resonance at a first natural cavity frequency which corresponds to some higher mode order. In particular, the solid line of FIG. 6b demonstrates that the component of the pressure field within the duct 12 at adjacent modes to that lower mode which excites the deep cavity embodiment into resonance is attenuated by more than 20 dB for all of the lower mode order that lie between 1 and 10. On the other hand, the broken line of FIG. 6b demonstrates that the rejection ratio of a deep cavity embodiment can be somewhat degraded due to simultaneous cavity resonance at a first natural frequency which corresponds to (or nearly corresponds to) a higher order modal component which is present in the duct pressure field. For example, and as previously described, when the deep cavity realization which produces the characteristics depicted in FIGS. 5a and 5b is tuned for resonance at the duct order 4 (by supplying an appropriate gas mixture) the cavity pressure transfer with respect to acoustic energy at one of the higher duct modes (mode number 13) is approximately 18 dB less than that presented to the acoustic energy at mode order 4. Since, in the absence of resonance in a corresponding first natural frequency, that particular deep cavity embodiment would attenuate all other modal components of the duct pressure field by more than approximately 30 dB, some degradation can occur, especially if the corresponding higher order modal component of the duct pressure field is of an amplitude substantially greater than that present at the lower mode order to which the cavity is tuned.

In view of the above-described characteristics of shallow and deep filter cavity embodiments of the invention, it should be recognized that, depending on the situation presented by the dimensions of the duct in which the pressure pattern is to be resolved into modal components, the frequency characteristics of the acoustic energy which propagates through the duct, and the desired system resolution, either a shallow cavity filter embodiment or a deep cavity filter embodiment that is dimensioned in one of the two above-described manners may provide satisfactory modal resolution. Further, it should be recognized that in such embodiments of the invention, the cavity radius R and the cavity length d can be judiciously selected in accordance with the previously set forth mathematical relationships to optimize the performance of a particular embodiment. For example, with respect to the above-described embodiment of a deep filter cavity which is dimensioned to be excited into resonance at a second natural frequency by each lower order duct mode when the cavity is filled with the gas mixture having a sonic velocity that exceeds that of air, the duct dimension d can be selected not only so that the sonic velocity of a mixture of available gasses excites the cavity into resonance at the lower order duct modes, but also selected such that the pressure transfer ratio at corresponding higher duct modes is minimized.

On the other hand, it should be recognized that embodiments of the invention employing a single one of the above described shallow and deep filter cavities may not provide a desired resolution at lower order duct modes for a particular application of the invention. In such situations, cascading several identical shallow filter cavities along the length of the duct 12 to effect a configuration which corresponds to cascaded electrical filter stages will often provide the necessary resolution since the pressure transfer characteristic of such a cascaded arrangement is substantially equal to the transfer characteristics of a single cavity multiplied by the number of stages (i.e., the number of cavities). Alternatively, an acoustic filter embodiment such as that depicted in FIG. 7 can be employed.

Figure 7:
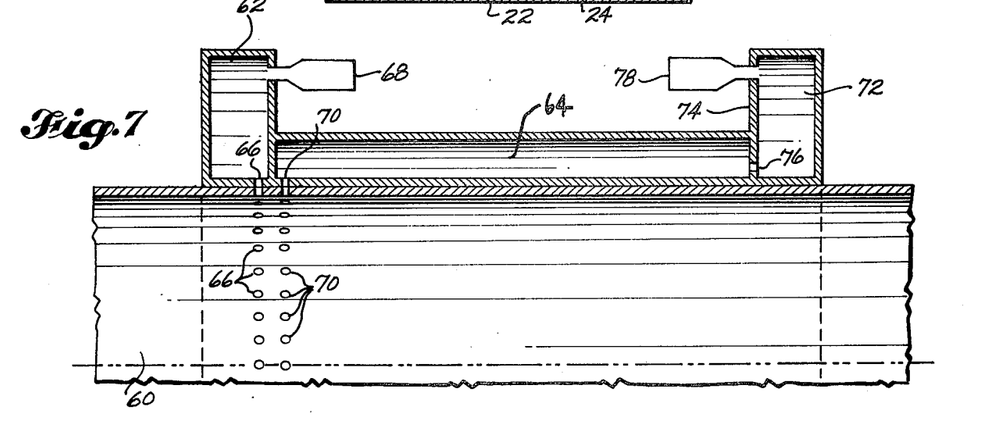
FIG. 7 depicts an acoustic filter which can be utilized in the acoustic measurement system of FIG. 1 wherein three separate filter cavities are realized to provide resolution of both low and high order duct modes.

In the arrangement of FIG. 7, two separate filter cavities are utilized for respectively determining the higher and lower order modal components of the acoustic pressure field within a cylindrical duct 60. In particular, the higher order modal components, i.e., those which excite a shallow cavity into resonance at a first natural frequency when the cavity is filled with a gas mixture having a sonic velocity that is equal to or less than that of a known gas such as hydrogen, are resolved within a cavity 62 and the lower order duct modes are resolved within a deep cavity 64.

In the filter embodiment depicted in FIG. 7, the shallow cavity 62 is dimensioned and arranged as previously described herein with a series of openings 66 that exhibit a relatively high acoustic impedance and a relatively high resistance to fluid flow coupling energy from the duct 60 into the shallow cavity 62. Additionally, for structural simplicity, the shallow cavity 62 of FIG. 7 is located immediately adjacent to the deep cavity 64 with the number of circumferentially spaced apart acoustic detectors or microphones 68 being acoustically coupled to the cavity 62 at a position proximate to the cavity wall that is oppositely disposed to the surface of the duct 60.

Viewing the cavity 62 of the arrangement depicted in FIG. 7, it can be noted that, with respect to the filter cavity 24 of FIGS. 1 and 3, the orientation of the cavity 62 relative to the duct which contains the acoustic pressure pattern is effectively rotated by 90°. In particular, the openings 66 and acoustic detectors 68 are respectively located in the shortest and longest cavity walls in the embodiment of FIG. 7 whereas in the embodiment of FIGS. 1 and 3, the openings 26 and acoustic detectors 50 are respectively located in one of the longer cavity walls and one of the shorter cavity walls. Such structural variation does not affect previously described operation of an acoustic cavity and the previously set forth mathematical relations provide the approximate design criteria. Thus, in the embodiment of FIG. 7, the cavity 62 is dimensioned and arranged as previously described herein.

The cavity 64 of the embodiment of FIG. 7 is acoustically coupled to the duct 60 by a second series of openings 70 wherein each of the openings are dimensioned to exhibit a relatively high acoustic impedance and relatively high resistance to fluid flow. The length of the cavity 64 is dimensioned such that the cavity 64 is of the previously discussed deep cavity variety wherein the cavity is excited into resonance in response to each of the lower order duct modes when the cavity 64 is filled with the gas mixture having a relatively high sonic velocity, e.g., the previously described $H_2 - CO_2$ mixture having approximately 2 to 6 percent $CO_2$ by volume.

To prevent the previously discussed higher mode acoustic signals that are coupled into such a deep filter cavity due to resonance of such a cavity at both a first and a second natural frequency, acoustic detectors or microphones are not directly coupled to the cavity 64, but are coupled to a third filter cavity 72. More specifically, the cavity 72 is located immediately adjacent to the deep cavity 64 with a common radially extending boundary wall 74 separating the cavities 64 and 72. A plurality of circumferentially spaced apart openings are located in the boundary wall 74 at a position proximate to the surface of the duct 60 to couple acoustic energy from the cavity 64 into the cavity 72. A number of acoustic detectors or microphones 78 are located near the opposite end of the cavity 72 for sensing the acoustic energy which propagates through the cavity 64 and into the cavity 72 via the openings 76. For example, as is depicted in FIG. 7, the microphones 78 are coupled to the cavity 72 through the radially extending boundary walls 74 at a position near the outwardly located boundary of the cavity 72.

The cavity 72 is dimensioned and arranged to effectively serve as a lowpass filter to thereby couple acoustic signals that are induced into the cavity 64 by resonance at a second natural frequency to the acoustic detectors 78 while substantially attentuating any acoustic signals induced into the cavity 64 due to resonance at an associated first natural frequency. Thus, as the composition of the gas mixture within the cavity 64 is controlled to cause the cavity 64 to resonate in response to each of the lower order modes (e.g., in the manner depicted in FIGS. 5a and 5b), the filter cavity 72 effectively eliminates extraneous signals that result from resonance of the cavity 64 at a first natural frequency (e.g., the extraneous signal at mode order 13 when the deep cavity embodiment of FIG. 5 is tuned for resonance at mode order 4).

As described relative to the shallow cavity embodiments of the invention, properly dimensioning a deep cavity can result in resonance at lower mode orders when such a cavity is filled with the gas having a sonic velocity less than that of air (the gas within the duct). Further, from the previous description of such deep cavities and FIG. 4b, it can be recalled that such a shallow cavity exhibits rather "broadband" filter characteristics in that, although higher order modes of the duct pressure filed are attenuated within such a cavity, the lower order modal components are not substantially attenuated (i.e., mode orders 0 and 5 in FIG. 4b). Accordingly, it can be recognized that the low pass filter cavity 72 of the embodiment depicted in FIG. 7 can be realized by such a shallow cavity which is dimensioned for resonance at a second natural frequency that corresponds to the approximate midpoint of the range of lower duct modes that is to be resolved within the filter cavity 64. In particular, the cavity 72 is preferably dimensioned so that a satisfactory pressure transfer characteristic is obtained when the cavity 72 is filled with a particular gas mixture which has a sonic velocity less than that of air, e.g., pure $CO_2$. With respect to dimensioning cavity 72 to achieve the desired lowpass filter characteristics, Equations 1 and 3 can be utilized to select suitable values of the cavity parameters d and R which satisfy the shallow cavity constraint while providing the desired filter characteristic. Further, to provide a symmetrical filter characteristics, it can be shown from Equation 2 that the R and d dimension of cavity 72 should be selected such that:

$$m_c = R[(\omega^2/c^2) - (\pi^2 d^2)]^{\frac{1}{2}}$$

where $m_c$ is the midpoint of the range of lower order modal components that are to be resolved within the cavity 64, i.e., $m_c$ is equal to $m_m/2$ where $m_m$ is the highest order modal component of the lower order duct modes, and c is the sonic velocity of the gas within the cavity 72. Even further, it can be recognized from Equation 1 that the desired lowpass filter characteristics can best be effected by dimensioning and arranging the openings 76 to exhibit as low a value of acoustic impedance (Z) as possible while maintaining the acoustic impedance Z at a value sufficient to prevent significant pressure perturbations in the cavity 64. In this respect, in one realization of the embodiment of FIG. 7, the openings 66 and 70 are dimensioned and arranged to exhibit an acoustic impedance of approximately 100 $\pi_0 c$, where $\pi_0$ and c are the density and sonic velocity of air, and the openings 76 are dimensioned and arranged to exhibit an acoustic impedance of approximately 20 $\pi_0 c$.

Turning now to the number of acoustic detectors or microphones 50, 68 and 78 that are employed in the above-described embodiments of the invention, it should first be noted that at least two acoustic detectors are necessary to determine the pressure values that are associated with the positive and negative values of each mode order m. Further, it should be recognized that two acoustic detectors or microphones which are mounted in a fixed spaced apart orientation around the circumference of the associated filter cavity will not necessarily provide sufficient pressure information to enable the determination of the two pressures associated with the positive and negative value of the modal order being resolved. In particular, when the pressures associated with the positive and negative value of any particular mode order are equal in amplitude, a standing wave pattern is present within the duct. If, only two acoustic detectors are employed in an embodiment of the invention and both of the detectors are positioned near a pressure node of such a standing wave pattern, the signal information provided by the detectors will not be sufficient to provide the two pressures associated with the positive and negative values of the corresponding mode order. Although, this problem can be eliminated by utilizing two acoustic detectors wherein one of the detectors can be selectively positioned about the cavity wall so that the detectors are separated by an angle of 90°/m where m is the order of the modal component being resolved, such a configuration greatly increases the structural complexity of the acoustic measurement system and greatly increases the time required to ascertain the modal structure of the duct pressure pattern. Accordingly, in accordance with this invention, more than two microphones 50, 68 and 78 are preferably employed in the previously described embodiments of the invention with such acoustic detectors being spaced from one another over approximately one quadrant of the associated filter cavity.

More specifically, consider the general situation in which a plurality of n microphones are utilized in a filter cavity of the invention with each of the microphones being mounted at a circumferential position $\theta_i$, i = 1, 2, ..., n relative to a radial reference coordinate wherein $\theta_{i+1} - \theta_i$ is not necessarily equal to $\theta_{i+2} - \theta_{i+1}$ for all i between one and (n − 2). The acoustic pressure coupled to each of these detectors when the associated cavity is tuned to resonate in response to a particular modal component can be shown to be:

$$p_i = A_m e^{jkR\theta_i} + A_{-m} e^{-jkR\theta_i}$$

where j is equal to $-\sqrt{-1}$, $\theta_i$ is the circumferential position of the microphone, k is equal to $\omega$ divided by the sonic velocity c that causes the associated cavity to resonate at the mode order under consideration and $A_m$ and $A_{-m}$ are the pressure coefficients associated with the positive and negative values of this mode order.

Examining Equation 4, it can be seen that each of quantities except the sought after pressure coefficients are known. Thus, when the number of detectors n is greater than 2 and the detectors are unequally spaced apart from one another, the microphones effectively supply an overdetermined system of n equations in two unknowns. Solving this system of equations by known mathematical techniques such as a least squares regression yields the appropriate values of the pressure constants even though one of the microphones or acoustic detectors supplies somewhat erroneous signal information because of, for example, system calibration errors or the microphone being located near a pressure node of a standing wave pattern.

Various methods and apparatus can be employed for ascertaining the desired amplitude coefficients from the signal information supplied by the acoustic detectors or microphones with such apparatus including means for sensing the relative phase and amplitude of the microphone signals to supply the information reqired for the solution of the above-mentioned system of equations. For example, by recording the signal supplied by the microphone (e.g., with a conventional oscilloscope), the system operator can manually determine the phase and amplitude information required for a solution of such a system of equations. On the other hand, an automated solution can be effected by computation apparatus such as the signal processor 52 of FIG. 1.

In the signal processor 52 of FIG. 1, the signal supplied by each microphone 50 is coupled to one input terminal of a multiplier circuit 54 and to one input terminal of a multiplier circuit 56. The second input terminal of the multipliers 54 and 56 are respectively coupled to output terminals of a reference generator 58 which supplies two signals at a frequency which corresponds to the frequency of the primary signal component that propagates within the duct 12 with the two signals supplied by the reference generator 58 being in phase quadrature (denoted by 0° and 90° in FIG. 1). In this respect, the 0° signal supplied by the reference generator 58 is preferably derived directly from the acoustic signal within the duct 12 by use of an additional microphone or other devices which can be mounted within the duct 12 or the cavity 24. In such a case, the quadrature signal can then be produced by employing conventional phase shifting techniques.

The multiplier circuits 54 and 56 can be conventional analog circuits, or in a situation in which the signal processor 52 is to be realized by digital circuitry, analog to digital conversion (not shown in FIG. 1) can be utilized to supply the multiplier circuits 54 and 56 with a digital signal representative of each microphone signal. In any case, each pair of multiplier circuits 54 and 56 that are associated with a particular microphone 50 supply two DC signals that represent the pressure signal supplied by the associated microphone 50 in the manner set forth by Equation 4. These DC signals are coupled to a computational unit 58 which is preferably a digital microprocessor circuit that is programmed to solve the previously described over-determined system of equations by conventional techniques such as matrix inversion and the desired pressure coefficients that are associated with the positive and negative values of the mode order being determined are displayed on an indicator 60 which can be a conventional printer device or display device such as a number of seven segment light-emitting diode displays.

Various measurements are facilitated by the invention. For example, the transient modal distributions of the duct associated with the filter arrangement can be ascertained by adjusting the gas mixture to cause cavity resonance at a mode of interest and then exciting the cavity with acoustic energy. By repetitively adjusting the composition of the gas mixture for resonance at each modal component of interest and exciting the duct, the transient behavior of the duct will be obtained.

Figure 8:
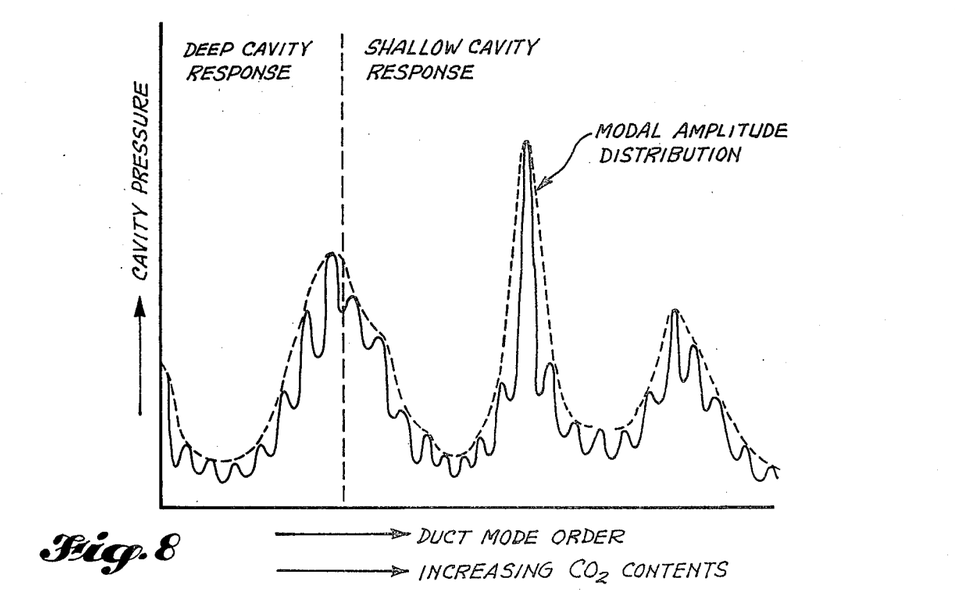
FIG. 8 graphically depicts a typical modal amplitude distribution which is obtained through the operation of this invention.

Further, the steady state modal distribution can be obtained by continuously varying the composition of the gas mixture and recording the pressure values supplied by the signal processor unit. An example of such a modal distribution is illustrated in FIG. 8 which depicts a typical modal distribution obtained with a filter embodiment of the type depicted in FIG. 7 when the gas mixture is slowly varied between a composition of pure Hydrogen to a composition of approximately 60% Carbon Dioxide and 40% Hydrogen (by volume).

It will be recognized by those skilled in the art that the embodiments of the invention described herein are exemplary in nature and that various modifications can be made without exceeding the scope and the spirit of the invention. For example, although the invention has been described with annular cavities circumferentially surrounding an air inlet duct of a gas turbine installation, the invention can be utilized in virtually any situation in which a complex acoustic pressure pattern is induced in a duct, e.g., an exhaust duct of a gas turbine installation. Further, since the mathematical relationships disclosed herein assume that the radial cavity dimension h is much less than the mean radius R of the annular cavities, the invention can be embodied as one or more circumferentially spaced apart axially extending cavities in situations in which it is desirable or necessary to determine the axial modes associated with the duct pressure pattern.

Those skilled in the art will also recognize that, although the invention has been described in the context of a variable composition gas mixture of hydrogen and carbon dioxide, various other gases such as helium can be utilized as the gas component having a sonic velocity greater than air and various gasses such as propane can be utilized as the gasseous component having a sonic velocity less than that of air. Further, in embodiments of the invention which do not utilize a deep cavity dimensioned for resonance when filled with a gas mixture having a sonic velocity less than that of air, air can be mixed with a gas having a higher sonic velocity (e.g., helium) to provide the necessary sonic velocity within the filter cavities in the invention.

In addition, and as previously noted, various signal processing circuits can be utilized as the signal processor 52 to detect the pressure amplitude associated with the positive and negative values of each mode order from the pressure signals supplied by the acoustic detectors. Similarly, various conventional apparatus can be utilized to supply and mix the gasses employed and various conventional devices can be used to determine the sonic velocity within the filter cavities.

The embodiments of the invention in which an exclusive property or privilege is claimed are defined as follows:

1. An acoustic measurement system for determining the modal structure of an acoustic pressure field within a duct comprising:
  an acoustic filter including at least one acoustic cavity, said acoustic filter in acoustic communication with said duct to couple sound energy from said duct to each of said acoustic cavities, each of said acoustic cavities being dimensioned and arranged to exhibit resonance in response to a modal component of said acoustic pressure pattern within said duct when the velocity of sound within each of said cavities is established at a predetermined value;
  gas supply means for supplying a mixture of gasses to each of said acoustic cavities of said acoustic filter, said gas supply means including means for varying the composition of said gas mixture supplied to said acoustic cavities to selectively tune said filter for resonance at a plurality of modal components of said acoustic pressure field; and
  acoustic detector means mounted in acoustic communication with said acoustic filter, said acoustic detector means supplying a signal representative of the acoustic pressure within said acoustic cavities to provide an indication of the amplitude of the modal component of said pressure field which excites said cavities into resonance.

2. The acoustic measurement system of claim 1 wherein said duct is substantially cylindrical and said acoustic filter includes a single annular cavity circumferentially surrounding said duct, said single annular cavity being defined by first and second spaced apart walls extending radially outward from said duct and a cylindrical wall concentrically surrounding said duct and interconnecting said first and second radially extending walls, said duct including a plurality of circumferentially spaced apart openings located proximate to said first radially extending wall of said single cavity for maintaining said duct in acoustic communication with said cavity, each of said openings being configured and arranged for exhibiting a relatively high acoustic impedance and a relatively high resistance to fluid flow, said acoustic detector means being mounted to said second radially extending wall of said single cavity and being in acoustic communication with said cavity.

3. The acoustic measurement system of claim 2 wherein said single cavity is dimensioned and arranged for resonance at a first natural frequency in response to modal components of said pressure field within said duct of mode order that exceeds a predetermined mode order m, and wherein said single cavity is dimensioned and arranged for resonance at a second natural frequency in response to modal components of said duct pressure field which do not exceed said predetermined mode order m.

4. The acoustic measurement system of claim 3 wherein said single cavity is further dimensioned and arranged for resonance at a first natural frequency in response to modal components of mode order greater than a predetermined mode order m, when said cavity is supplied with a gas mixture having a sonic velocity that exceeds the sonic velocity of the gas within said duct and is dimensioned and arranged for resonance at a second natural frequency in response to modal components of a mode order which does not exceed said predetermined mode order m, when said cavity is supplied with a gas mixture having a sonic velocity that is less than the sonic velocity of the gas within said duct, said gas supply means including means for selectively varying the composition of said gas mixture supplied to said single cavity to selectively establish the sonic velocity within said cavity for resonance at a plurality of said modal components of said pressure field within said duct.

5. The acoustic measurement system of claim 3 wherein said single cavity is dimensioned and arranged for resonance at a second natural frequency in response to modal components of mode orders that do not exceed a predetermined mode order m, when the sonic velocity of the gas mixture supplied to said cavity exceeds the sonic velocity of the gas within said duct, said single cavity being further dimensioned and arranged for resonance at a first natural frequency in response to modal components of mode order exceeding said predetermined mode order m, when the sonic velocity of the gas mixture supplied to said single cavity exceeds the sonic velocity of the gas within said duct and is less than the sonic velocity which causes resonance at said second natural frequency for said modal components of mode orders that do not exceed said predetermined mode order m, said gas supply means including means for selectively varying the composition of said gas mixture supplied to said single cavity to selectively establish the sonic velocity within said cavity for resonance at a plurality of said modal components of said pressure field within said duct.

6. The acoustic measurement system of claim 1 wherein said duct is substantially cylindrical and said acoustic filter includes first, second and third annular cavities circumferentially surrounding said duct, said first annular cavity being acoustically coupled to the interior region of said duct by a first plurality of circumferentially spaced apart openings in said duct, said first cavity being dimensioned for resonance at a first natural frequency corresponding to a modal component of the pressure field within said duct of mode order greater than a predetermined mode order m when said first cavity is supplied with a predetermined gas mixture having a sonic velocity that exceeds the sonic velocity of the gas within said duct, said second annular cavity being acoustically coupled to the interior region of said duct by a second plurality of circumferentially spaced apart openings in said duct, said second cavity being dimensioned for resonance at a second natural frequency corresponding to a modal component of the pressure field within said duct of mode order that does not exceed that of said predetermined mode order m, when said second cavity is supplied with a predetermined gas mixture having a sonic velocity that exceeds both the sonic velocity of said gas within said duct and the sonic velocity of the gas mixture supplied to said first cavity, said third cavity positioned immediately adjacent to said second cavity with said second cavity being acoustically coupled to said third cavity by a third plurality of circumferentially spaced apart openings that interconnect said second and third cavities, said third cavity being filled with a gas having a sonic velocity less than that of the gas within said duct, said third cavity being dimensioned to operate as a low pass filter for attenuating pressure signals induced in said second cavities by modal components of said duct pressure field that are of a mode order that exceeds said predetermined mode order m, said acoustic detector means including first pressure sensing means acoustically coupled to said first cavity for supplying signals representative of modal components of mode order exceeding said predetermined mode order m, and including second pressure sensing means acoustically coupled to said third cavity for supplying signals representative of modal components of mode order not exceeding said predetermined mode order m, said gas supply means including means for selectively varying the sonic velocity of the gas mixture within said first and second cavities for tuning said first and second cavities for resonance in response to a plurality of said modal components.

* * * * *